United States Patent [19]

Mann

[11] Patent Number: 5,491,219
[45] Date of Patent: Feb. 13, 1996

[54] FERRITIN WITH FERRIMAGNETICALLY ORDERED FERRITE CORE AND METHOD TECHNICAL FIELD

[75] Inventor: Stephen Mann, Bath, United Kingdom

[73] Assignee: Protein Magnetics, San Luis Obispo, Calif.

[21] Appl. No.: 76,718

[22] Filed: Jun. 11, 1993

[51] Int. Cl.[6] .......................... C07K 16/00; C04B 35/00; C04B 35/26; H01F 1/03
[52] U.S. Cl. .................................. 530/391.1; 530/391.7; 436/518; 252/62.51 R; 252/62.62; 148/100; 148/105
[58] Field of Search ................................. 436/518; 424/9; 428/457, 402; 427/2, 2.1, 2.11; 148/100, 105; 252/62.51, 62.62; 530/391.1, 391.7

[56] References Cited

U.S. PATENT DOCUMENTS

| 3,966,510 | 6/1976 | Aonuma et al. | 148/105 |
| 4,096,316 | 6/1978 | Tamai et al. | 428/457 |
| 4,672,040 | 6/1987 | Josephson | 436/526 |
| 4,735,796 | 4/1988 | Gordon | 424/9 |
| 4,814,098 | 3/1989 | Inada et al. | 252/62.51 |
| 5,043,101 | 8/1991 | Gordon | 252/408.1 |

OTHER PUBLICATIONS

Meldrum, et al., "Magnetoferritin: In Vitro Synthesis of a Novel Magnetic Protein", *Science*, vol. 257, 24 Jul. 1992, pp. 522–523.

Rohrer et al., *The Journal of Biological Chemistry*, vol. 262, No. 28, issued Oct. 5, 1987, pp. 13385–13387.

*Primary Examiner*—W. Gary Jones
*Assistant Examiner*—Bradley L. Sisson
*Attorney, Agent, or Firm*—Coudert Brothers

[57] ABSTRACT

Biocompatability and orders greater magnetic responsiveness characterize a uniquely useful new product, magnetoferritin, comprising ferritin having a ferrimagnetically ordered ferrite core in place of the naturally occurring ferrihydrite core. A method of preparation is disclosed.

11 Claims, No Drawings

FERRITIN WITH FERRIMAGNETICALLY ORDERED FERRITE CORE AND METHOD TECHNICAL FIELD

TECHNICAL FIELD

This invention has to do with the preparation of novel proteins useful in imaging of biological tissue, separations through labeling of cells and antibodies, and in a host of applications where magnetic properties are advantageously employed on a nanometer scale. More particularly, the invention provides a novel product: ferritin with a ferrimagnetically ordered, ferrite core. This product, sometimes referred to herein as magnetoferritin, affords a 10,000 fold and greater improvement in body or room temperature magnetic properties over naturally occurring ferritin, which has a paramagnetic core rather than the superparamagnetic core obtained in the invention.

BACKGROUND

While the core of naturally occurring ferritin is comprised of the hydrous iron oxide ferrihydrite, the ferrimagnetic core is typically comprised of the iron-oxide ferrite magnetite, $Fe_3O_4$, or maghemite, $\gamma-Fe_2O_3$, or an intermediate composition. Magnetite and maghemite are members of a series continuum of solid solutions. For ease of description reference will be made to magnetite as inclusive of maghemite as the ferrimagnetic constituent of the ferritin core in the compositions of the invention. The core can also be comprised of other transition metal ferrites.

Ferritin, a protein naturally occurring in bacteria, fungi, plants, invertebrates and vertebrates including humans, is characterized by an ability to sequester and store iron in a bioavailable form. Chemically, the protein is a quaternary structure of 24 polypeptide units assembled into a spherical shell having an internal cavity about 8–10 nm in its longest dimension and penetrated by two types of intersubunit channels. In naturally occurring ferritin, the cavity contains up to 4500 iron atoms as a mineral core of the hydrous iron oxide ferrihydrite which is paramagnetic at ambient temperature. To my knowledge no one has substituted into the cavity of ferritin a ferrimagnetically ordered ferrite core with improved magnetic characteristics.

SUMMARY OF THE INVENTION

It is an object therefore of the present invention to provide a novel product and preparation therefor. It is another object to provide a product comprising a ferrimagnetically ordered, ferrite core within ferritin product, and method therefor. It is a further object to provide a magnetoferritin product having a magnetite ($Fe_3O_4$) core.

These and other objects of the invention are realized in a modified naturally occurring ferritin having a ferrimagnetic core in lieu of its normal hydrous iron oxide ferrihydrite core. The ferrimagnetic core typically comprises magnetite. The product core constituent in the invention modified ferritin in 1 mg/ml aqueous solution is black rather than the reddish brown characteristic of the iron oxide ferrihydrite core of naturally occurring ferritin. The structure of the invention product core is a face-centered cubic, spinel structure corresponding to magnetite and maghemite, whereas the hydrous iron oxide ferrihydrite is poorly crystalline with a hexagonal close packed structure. The magnetic properties of the modified ferritin are 10,000 times that of the naturally occurring molecules with the same number of iron atoms per molecule. Ferritin with 1000 iron atoms in a ferrite core has a magnetic dipole moment per particle of $10^{21}$ ergs/gauss in a 1000 gauss magnetic field, whereas ferritin with 1000 iron atoms in a magnetite core has a magnetic dipole moment per particle of $10^{-17}$ ergs/gauss in a 1000 gauss magnetic field.

Ferritin with a magnetite core in 1 mg/ml solution in a test tube is perceptibly attracted to a samarium-cobalt permanent magnet touching the outside of a test tube at the level of the ferritin solution. Naturally occurring ferritin with its ferrihydrite core is not attracted under the same conditions.

Other magnetic minerals having similar structures to magnetite, including divalent transition metal ferrites, $MeFe_2O_4$, wherein Me is Ti, Mn, Cr, Co, Ni or Cu, and transition metal sulfides such as $Fe_3S_4$ and FeS, may be substituted into ferritin as well.

Accordingly, the invention provides ferritin product having a ferrimagnetically ordered ferrite core. Typically, the ferrite product has a magnetic dipole moment per particle of greater than $10^{-17}$ gauss, the ferrite core comprises magnetite, maghemite, or the ferrite core has the formula $MeFe_2O_4$, and Me is a divalent transition metal selected from Ti, Cr, Mn, Co, Ni and Cu, or the ferrite core is a transition metal sulfide such as $Fe_3S_4$ or FeS. The ferrite core comprises a minimum of 10 and preferably 100 metal atoms.

In preferred form, the ferritin product core comprises magnetite, has a face-centered cubic spinel crystal structure in the size of up to 10 nm, has a magnetic dipole moment per particle above $10^{-17}$ ergs/gauss, has a blackish appearance in dilute aqueous solution and is perceptibly attracted to a samarium-cobalt permanent magnet.

The invention further contemplates the method of preparing a ferritin product having a ferrimagnetically ordered ferrite core, including removing naturally occurring ferrihydrite iron core from the ferritin cavity to form apoferritin in aqueous solution, incorporating ferrimagnetically ordered ferrite by oxidation-precipitating the said ferrite from an aqueous Fe(II) solution into said cavity, preferably selecting a water soluble Fe(II) salt as the source of iron for said ferrite core, chemically or electrochemically oxidizing the iron, selecting air, trimethylene oxide or metal iodate salt as chemical oxidants for the iron, preferably having said Fe(II) solution is added incrementally to said apoferritin solution while sparging air into said combined solutions, and selecting bacteria, fungi, plants, invertebrates, recombinant ferritin or site-directed ferritin mutants as the source of ferritin.

EXAMPLE

Magnetite was placed into the ferritin cavity by slow aerial oxidation of an aqueous solution of Fe(II) at pH 8.5 and about 60° C. to precipitate $Fe_3O_4$ in the presence of mammalian apoferritin. In addition to or in place of air as oxidant, other chemical oxidants can be used for the Fe(II) oxidation step, including, metal iodate salts, and trimethylamine oxide, or electrochemical means.

Apoferritin, i.e. ferritin without its normal iron oxide ferrihydrite core, was prepared from naturally occurring mammalian ferritin as follows; Horse spleen ferritin (Boeringer, Cd-free, 50 mg/ml) was dialyzed under nitrogen flow against thioglycolic acid in a sodium acetate buffer at pH 4.5, followed by repeated dialysis against 0.15M saline, to ensure removal of the naturally occurring ferrihydrite iron in the ferritin. A portion of the resulting 1μM apoferritin solution, buffered to 8.5 pH with O.05M AMPSO (3-[1,1- dimethyl-2-hydroxyethyl)-2-amino]-2-hydroxypropane sulfonic acid; ex Sigma) was equilibrated in a water bath at 55°–60° C. while being purged with argon.

4cm$^3$ of the apoferritin thus prepared was subjected to multiple additions of a solution of Fe(II) prepared by the solution in deaerated water of ferrous ammonium sulfate [$NH_4)_2SO_4.FeSO_4.6H_2O$] to a concentration of 24 mM. Ten additions of the ferrous solution were made to the protein solution under argon flow, 0.05 ml being added at 20 minute intervals until a total of 0.5ml was added. A very slow oxidation rate was achieved by sparging air into the reaction solution via a Pasteur Pipette.

Control

A Control reaction was carried out in an analogous manner to the protein loading example above, by the addition of the ferrous solution in aliquots to 4cm$^3$ of a deaerated solution of NaCl, 0.004M, buffered to 8.5 pH buffer at 55°–60° C.

Analytical Evaluation

Samples of Example 1 and the Control were taken immediately upon completion of the addition of the Fe(II) for transmission electron microscopy (TEM). Other samples were taken from a solution portion left open to air.

The TEM samples were prepared by placing a carbon-coated, formvar-covered copper electron microscope grid on a drop of the reaction solution. Excess solution was removed after a few minutes by drawing lint-free paper over the grid which was allowed to air dry. Negative staining of the protein grids was achieved by placing a protein-loaded grid on a drop of 1% by weight uranyl acetate solution for approximately two minutes. Excess solution was removed as above. The protein-loaded grids were washed before examination by passage through the meniscus of distilled water to limit the artificial saline background on the grids. To confirm that all diffraction patterns were obtained from the mineralized cores, Energy Dispersive X-Ray Analysis (EDX) was performed on the area selected for diffraction, and the corresponding transmitted image was recorded. The possibility that saline or non-specific oxidation were contributing to the protein core electron diffraction patterns was thus excluded.

X-Ray Diffraction analysis (XRD) was also performed on samples obtained by centrifuging portions of the reaction solution, decanting off the mother liquor and finally drying the residual solids under vacuum desiccation.

In the Control, addition of the initial ferrous solution aliquots to the buffer solution generated a white precipitate. With slow oxidation this was replaced by a green gelatinous precipitate. After approximately one hour, a blackish discoloration was noted and, on completion of the ferrous solution additions, a black precipitate which was sensitive to an applied magnetic field settled out of solution, leaving a colorless supernatant. Repetition of the procedure in the presence of apoferritin resulted in an initial cloudy appearance of the solution, with a blackish discoloration developing after about one hour. No green colored intermediate appeared during this process. After all additions of the Fe(II) solution had been made, the bulk solution was blackish in color and no precipitate was seen.

TEM examination of the Example and Control preparations revealed crystals of remarkably different size and morphology. The Control solution contained a heterogeneous population of crystals of size range up to 10 nm. A variety of different morphologies consistent with magnetite/maghemite were observed, ranging from poorly defined spherical crystallites, to cubic and cubo-octahedral. Some needle-like crystals were also noted, and were identified on the basis of their morphologies as goethite By contrast, in the Example, the protein core comprised crystallites presenting a homogeneous population of particles, spherical in shape and displaying a narrow size distribution: mean core size 6.1 nm, standard deviation 1.2 nm. These crystals are comparable in size and morphology to the ferrihydrite ($5Fe_2O_3.9H_2O$) cores of native ferritin: mean core diameter 7.8 nm, standard deviation 0.6 nm. Negative staining of the Example protein grids confirmed that the particles were located within the protein cage. The restricted volume and environment provided by the apoferritin shell controlled both the size and morphology of the crystals generated within.

Electron diffraction identified the crystals formed in the Example protein and Control reactions to be either crystalline magnetite ($Fe_3O_4$) or maghemite ($\gamma$-$Fe_2O_3$) (Table 1). A distinction between magnetite and maghemite cannot be made solely on the basis of electron diffraction data. Both materials possess face-centered cubic spinel structures, vary little in their cell dimension, and are end members of a continuous series of solid solutions. Only weak superlattice lines present in the maghemite spectrum would definitively show the crystals to be maghemite rather than magnetite. These reflections are not of sufficient intensity to be recorded by electron diffraction. However, the experimental observations suggest that magnetite was formed under the anaerobic conditions of the experiment. The crystals produced initially were black in color (characteristic of magnetite) and oxidation readily occurred after exposure to an aerobic environment to give particles red/brown in color (characteristic of maghemite). That a magnetic iron oxide is formed within the protein rather than ferrihydrite is shown unequivocally from the diffraction data from the cores (Table 2). Not only do the patterns fit much better to magnetite than they do to ferrihydrite, but a line is observed at a d-value of 2,945Å; the largest d-value expected from ferrihydrite is at 2.50Å.

TABLE 1

Electron diffraction data from Example 1 and Control
Data is compared with d values expected for magnetite

| d VALUE CALCULATED (Å) | d VALUE THEORETICAL (Å) | I/I$_o$ |
|---|---|---|
| EXAMPLE 1-PROTEIN RECONSTITUTION: | | |
| 2.945 | 2.967 | 30 |
| 2.558 | 2.532 | 100 |
| 2.099 | 2.099 | 20 |
| 1.715 | 1.715 | 10 |
| 1.636 | 1.616 | 30 |
| 1.499 | 1.485 | 40 |
| CONTROL: | | |
| 4.81 | 4.85 | 8 |
| 3.016 | 2.967 | 30 |
| 2.528 | 2.532 | 100 |
| 2.086 | 2.099 | 20 |
| 1.722 | 1.715 | 10 |
| 1.621 | 1.616 | 30 |
| 1.484 | 1.485 | 40 |
| 1.286 | 1.281 | 10 |
| 1.094 | 1.093 | 12 |

TABLE 2

Comparison of the fit of the electron diffraction data from the protein cores to magnetite and ferrihydrite

| CALCULATED d VALUE (Å) | THEORETICAL d VALUE MAGNETITE (Å) | THEORETICAL d VALUE FERRIHYDRITE (Å) |
|---|---|---|
| 2.945[1] | 2.967 | |
| 2.558 | 2.532 | 2.50 |
| — | — | 2.21 |
| 2.099 | 2.099 | 1.96 |
| 1.715 | 1.715 | 1.72 |
| 1.636 | 1.616 | — |
| — | — | 1.51 |
| 1.499 | 1.485 | 1.48 |

[1]Note: Appearance of this diffraction line shows unequivocally that the protein cores in the Example are not ferrihydrite. The largest d value observed for ferrihydrite is 2.50Å. The diffraction data fit well to magnetite.

EDX analysis further verified that the particles are iron-containing minerals and that saline is not contributing to the diffraction patterns.

High resolution TEM studies (HRTEM) were also carried out on crystals formed in the Example and Control procedures. The observed lattice planes and interplanar angles correlate directly with predicted data for magnetite. Images from the magnetite control crystals showed lattice fringes running continuously and coherently over the total width of the individual particles including (111) type fringes (d111= 4.85Å), two sets of the (111) type at 70° to each other and one set of (002) type at 54° to these (d002=4.198Å). Both crystals are bound by (111) faces. These images are consistent with the intrinsic stability of (111) octahedral faces in magnetite. Also seen are (311) type planes, d311=2.532Å. Despite the very low contrast displayed by images of the magnetic ferritin cores, HRTEM images of the particles can still be recorded, showing the crystalline nature of the cores Also seen are ferritin cores displaying two sets of fringes corresponding to (111) and (002) planes at a spacing of 54°, two sets of (220) type planes, d220=2.967Å, with an angular separation of 60°, and one set of fringes corresponding to (220) planes.

Subsequent to preparation of magnetite in Control and Example solutions, the argon flow was discontinued and the reaction solutions were exposed to unrestricted oxygen. In the Control, no change in the appearance of the precipitate was observed, even after a period of two weeks. However, within a few minutes of exposing the Example protein solution to air, a color change from black to red/brown was observed.

Electron diffraction data from the oxidized protein cores showed patterns consistent with magnetite/maghemite. Although electron diffraction will not differentiate between magnetite and maghemite, color change observed on exposure of the sample to air (black-to-brown) is characteristic of the oxidation of magnetite to maghemite. X-Ray diffraction of the oxidized control crystals showed weak superlattice lines characteristic of maghemite. See Table 3:

TABLE 3

Electron diffraction data obtained from control crystals after oxidation

| d VALUE CALCULATED (Å) | d VALUE THEORETICAL ($\gamma Fe_2O_3$) (Å) | $I/I_o$ |
|---|---|---|
| 4.830 | 4.820 | 8 |
| 2.953 | 2.967 | 30 |
| 2.770 | 2.780 | 3 |
| 2.523 | 2.532 | 100 |
| 2.087 | 2.099 | 20 |
| 1.708 | 1.715 | 10 |
| 1.608 | 1.616 | 30 |
| 1.479 | 1.485 | 40 |
| 1.384 | 1.318 | 6 |
| 1.275 | 1.272 | 8 |
| 1.260 | 1.258 | 3 |

Evaluation Of Magnetic Properties

Magnetoferritin as produced in the foregoing Example has been evaluated for its magnetic properties. The magnetoferritin was placed in an applied magnetic field up to 5000 oersted at ambient temperature using a SQUID magnetometer. The magnetization was proportional to a Langevin function of H/T, with a magnetic dipole moment per particle of between $10^{-16}$ and $10^{-17}$ ergs/gauss. There was no magnetic hysteresis. This was consistent with magnetically ordered, superparamagnetic particles. Measurements of the magnetization at lower temperatures down to 4.2K indicated that the superparamagnetic blocking temperature was about 21K. These results are consistent with a magnetite/maghemite core in magnetoferritin. The atomic magnetic dipoles in magnetite are ferrimagnetically ordered below 580K. Very fine particles of magnetite, of the order of 20 nm or less, are superparamagnetic at ambient temperature. A superparamagnetic particle has a permanent magnetic dipole moment proportional to the number of iron atoms, but the orientation of the moment with respect to the crystallographic axes of the particle can fluctuate in time. When an ensemble of superparamagnetic particles are subjected to an external magnetic field, the particle moments tend to orient along the field direction with the average alignment a function of H/T. The alignment for superparamagnetic particles is much higher than that for paramagnetic particles, as in ferrihydrite. In paramagnetic particles the individual atomic magnetic dipoles in each particle tend to align along the field independently, whereas in superparamagnetic particles the atomic dipoles align as a single, larger entity. Assuming 1000 iron atoms in a core, the magnetization of magnetoferritin with a magnetite core would be 10,000 times greater in an applied field of 1000 oersted than the magnetization of ferritin with a ferrihydrite core.

While not wishing to be bound to any particular theory of the mechanism by which the magnetite is produced in the apoferritin to reconstitute the apoferritin as magnetoferritin it is believed that the precipitation of magnetite within ferritin proceeds via a ferric oxide, here ferrihydrite, intermediate as it has been shown that ferrihydrite is a potential precursor to magnetite. In the presence of an oxidizing agent, ferritin is catalytic in iron oxidation. In accord with a hypothesis concerning ferrioxidase behavior of ferritin deduced from XAS studies, on a low level and slow oxidation rate a small ferric core may initially form. Addition of an aliquot of ferrous solution will likely result in adsorption of Fe(II) to the ferric core; ferritin can uptake Fe(II) without oxidation and the pH is such that adsorption of metal ions can occur. Reaction may then occur between ferrous and ferric hydroxo complexes and magnetite precipitated via a dissolution/precipitation process. Growth of magnetic particles can then occur by formation of a ferric oxide layer on the existing $Fe_3O_4$ core, further adsorption of Fe(II) on that surface, and the subsequent transformation into $Fe_3O_4$.

The increase in magnetic susceptibility of the invention magnetoferritin opens many areas of application. Ferritin with a core of ferrimagnetically ordered ferrite such as magnetite or maghemite, as well as similar transition metal ferrites noted herein, provides a system of unique importance, combining the biocompatability of the ferritin molecule with the ferromagnetic and ferrimagnetic properties of the magnetic core. Applications of ferritin molecules labelled in such a manner include the following among others:

Separation of cells by electrophoretic methods. Such separation is currently limited under normal physiological conditions because of overlapping mobility distributions. Cell surface and cytoplasmic labelling of cell subpopulations with magnetic ferritin offers the possibility of greatly enhanced resolution;

Isolation of cells. Magnetic properties can be used in the isolation of specific types of cells. The separation and purification of cells labelled with antibody-coupled ferritin using magnetic field gradients offers the possibility of processing large numbers of cells for biochemical and immunological studies. Indeed, targeting of antibody-coupled ferritin may conceivably allow location of diseased tissue.

Markers. Subsequent to separation, the bound ferritin molecules can act as markers for specific sites on cell walls as imaged by TEM, such examination giving information on cell ultrastructure.

Immunolabeled ferritin molecules carrying cytoxic drugs or radioisotopes can be localized in certain tissue of the body through the influence of powerful externally applied magnets. Many of the reagents previously used for cell tagging suffer from a lack of stability or nonspecific interactions. The invention magnetoferritin is both chemically stable and entirely biocompatible.

NMR. NMR imaging permits the three-dimensional reconstruction of soft tissue in the body by targeting proton-bearing species present, principally water and fats. The localization of magnetic ferritin in particular areas of the body will enhance potential images.

Other noted magnetic minerals having similar structures to magnetite, including divalent transition metal ferrites, $MeFe_2O_4$, wherein Me is Ti, Cr, Mn, Co, Ni or Cu, and transition metal sulfides such as $Fe_3S_4$ and FeS, may be incorporated into apoferritin as well as magnetite and maghemite to form the invention product ferritin with a ferrimagnetically ordered ferrite core.

The foregoing objects are thus met.

I claim:

1. Ferritin product having a ferrimagnetically ordered core, in which said core comprises magnetite or maghemite, has a face-centered cubic spinel crystal structure in the size of up to 10 nm, has a magnetic dipole moment per particle above $10^{-17}$ ergs/gauss, has a blackish or red/brown appearance in dilute aqueous solution and is perceptibly attracted to a samarium-cobalt permanent magnet.

2. Ferritin product according to claim 1 wherein said ferrite core consists essentially of magnetite.

3. Ferritin product according to claim 1 wherein said ferrite core consists essentially of maghemite.

4. Ferritin product according to claim 1, in which said ferrite core comprises a minimum of 10 metal atoms.

5. Ferritin product according to claim 1, in which antibodies or other proteins are coupled to said ferritin product.

6. Method of preparing a ferritin product having a ferrimagnetically ordered ferrite core, in which said core comprises magnetite or maghemite, has a face-centered cubic spinel crystal structure in the size of up to 10 nm, and has a magnetic dipole moment per particle above $10^{-17}$ ergs/gauss, including removing naturally occurring ferrihydrite iron core from the ferritin cavity to form apoferritin in aqueous solution, incorporating the ferrimagnetically ordered ferrite by oxidation-precipitating the said ferrite from an aqueous Fe(II) solution into said cavity.

7. The method of claim 6, including also selecting a water soluble Fe(II) salt as the source of iron for said ferrite core.

8. The method according to claim 7, including also chemically or electrochemically oxidizing said iron.

9. The method according to claim 7, including also selecting air, trimethylamine oxide or iodate salt as chemical oxidants for said iron.

10. The method according to claim 6, in which said Fe(II) solution is added incrementally to said apoferritin solution while sparging air into said combined solutions.

11. The method according to claim 6, including also selecting bacteria, fungi, plants, invertebrates, vertebrates, recombinant or site-directed ferritin mutants as the source of ferritin.

* * * * *